(12) United States Patent
Bayer et al.

(10) Patent No.: US 6,447,764 B1
(45) Date of Patent: Sep. 10, 2002

(54) METHOD FOR ISOLATING ANIONIC ORGANIC SUBSTANCES FROM AQUEOUS SYSTEMS USING CATIONIC POLYMER NANOPARTICLES

(75) Inventors: Ernst Bayer; Hans Fritz, both of Tübingen (DE); Martin Maier, Carlsbad, CA (US); Jens Schewitz; Michael Gerster, both of Tübingen (DE)

(73) Assignee: Degussa AG, Trostberg (DE)

( * ) Notice: Subject to any disclaimer, the term of this patent is extended or adjusted under 35 U.S.C. 154(b) by 0 days.

(21) Appl. No.: 09/505,963

(22) Filed: Feb. 17, 2000

Related U.S. Application Data

(63) Continuation of application No. PCT/EP98/05340, filed on Aug. 21, 1998.

(30) Foreign Application Priority Data

Aug. 21, 1997 (DE) .......................................... 197 36 366

(51) Int. Cl.$^7$ ......................... A61K 31/74; A61K 35/00
(52) U.S. Cl. ...................................... 424/78.1; 424/124
(58) Field of Search ............................... 424/78.1, 489; 210/635

(56) References Cited

U.S. PATENT DOCUMENTS 6,090,288 A * 7/2000 Berglund et al. ........... 210/635

FOREIGN PATENT DOCUMENTS

| EP | 0 281 390 | * | 9/1988 |
| EP | 0 281 390 A2 | | 9/1988 |
| EP | 281390 | * | 9/1988 |
| FR | 2 691 969 | | 12/1993 |

OTHER PUBLICATIONS

Gerster et al. "A novel solid phase extraction system for oligonucleotides usig cationic nanoparticles" Innovation Perspect. Solid Phase Synth. comb. libr. Collect. Pap., Int. Symp., 5th (1999), Meeting Date 1977, 301–304, Epton ed.*

Liteanu et al., "Introduction to Use of Gradients," Gradient liquid Chromatography, pp. 125–132, John Wiley & Sons, New York (1974).*

Fritz, Hans et al., "Cationic Polystyrene Nanoparticles: Preparation and Characterization of a Model Drug Carrier System for Antisense Oligonucleotides", Journal of Colloid and Interface Science, vol. 195, pp. 272–288 (1997).

* cited by examiner

Primary Examiner—Thurman K. Page
Assistant Examiner—Blessing Fubara
(74) Attorney, Agent, or Firm—Nath & Associates PLLC; Gary M. Nath; Todd L. Juneau

(57) ABSTRACT

The invention relates to a method for isolating anionic organic substances from aqueous systems using polymer nanoparticles with cationic pH-sensitive surface groups. Extraction can be carried out directly from diluted solutions, biological media (blood plasma, serum, urine, etc.) and complex buffer systems (e.g. PCR preparations contain detergents) without prior derivatization of the samples or addition of binding buffers. After separation from the surrounding medium the conjugates of the corresponding substances and polymer nanoparticles obtained in this manner can be purified through additional washing steps and effectively desalinated. Owing to the pH-sensitivity of the basic surface groups, the bound substances can be released in a targeted manner after separation by modification of the pH of the medium. By using volatile bases contamination of the released samples with ionic residues can be avoided. By adding small quantities of SDS and acetonitrile during the separation stage, the sensitivity of the method can be raised further, especially when the substance to be isolated are present in low concentrations (<1 $\mu$mol/L). The method is a method of extraction with universal application, suitable for both low-molecular anionic compounds as well as peptides, nucleic acids and nucleic acid derivatives. Recovery rates are up to 100%.

12 Claims, No Drawings

METHOD FOR ISOLATING ANIONIC ORGANIC SUBSTANCES FROM AQUEOUS SYSTEMS USING CATIONIC POLYMER NANOPARTICLES

This application is a Continuation Application of international application PCT/EP98/05340 issued Aug. 21, 1998 contents of which are hereby incorporated in their entirety.

TECHNICAL FIELD

The present invention relates to a method for isolating organic compounds with anionic character from aqueous systems using cationic polymer nanoparticles.

BACKGROUND OF THE INVENTION

The isolation and characterization of anionic organic compounds represents a big challenge particularly in environmental analysis and in the fields of biotechnology. Frequently, compounds which are to be isolated are present in aqueous systems at high dilution and/or in combination with other classes of substances. Therefore, a suitable extraction method must fulfill the following requirements:

selectivity that is as high as possible no necessity of a previous derivatization of the substances to be isolated effective separability of the exracts from the aqueous system simple concentration and release of the isolated substances in high purity.

The quantitative detection of environmentally relevant and deleterious substances in the ground and water is becoming more important. Hence, it is of great interest to not only go below the limit of detection of the previous customary methods but to also obtain information on the exact composition of the substance mixtures for several classes of substances such as, for example, nitrophenols, chlorophenols and phenoxycarboxylic acids that can be present in drinking water or ground water as impurities.

Up to now, phenols and phenol derivatives have been mainly determined as a cumulative parameter according to German standard specification (DIN) 38409 part 16 (H16). This determination of the phenol index results from a color reaction with 4-aminoantipyrin and does not give any information on the composition of the sample but only on its total phenol content. Solid phase extraction methods with PR C-18 phases are also applied, among others, for isolating the substance classes of nitrophenols and chlorophenols. However, for this it is necessary to derivatize the samples before the actual extraction, for example, by the reaction with acetic anhydride. With different reactivity of the individual phenol derivatives, this additional reaction step can lead to a falsification of the results of the analysis. Similar problems arise with the extraction of phenoxycarboxylic acids that also have to be derivatized before the solid phase extraction.

The isolation of anionic organic systems in the form of peptides, nucleic acids and nucleic acid derivatives also plays an important role in the field of biological, pharmaceutical and medicinal applications. For example, synthetic oligonucleotides with their polyanionic character represent a new class of therapeutic substances that are employed, for example, in the antisense and antigen strategy for controlling gene expression. Usually, modified nucleic acids are used for this which are only composed of a small number of nucleotides of up to approximately 25 nucleotide units. In order to obtain information on the metabolism and the pharmakinetics of these active ingredients within the course of pre-clinical and clinical studies, it is necessary to isolate the employed nucleic acids and their degradation products from biological media such as blood, urine or cell extracts. In order to make them accessible for characterization by means of sensitive analytical methods, the substances should be present in high yield and purity after separation and, in particular, should not have any impurities due to foreign electrolytes.

Up to now, oligonucleotides and their derivatives have mainly been extracted from biological media via chromatography using ion exchange resins. The elution of the nucleic acids ensues after the separation of the serum components with buffers of high ionic strength. Consequently, the high salt content of the samples necessitates additional purification steps for de-salting in order to permit characterization of the material. The use of a two-stage solid phase extraction for isolating oligonucleotides from human blood plasma using a combination of ion exchange chromatography and reversed phase chromatography is described in J. M. Leeds, M. J. Graham, L. Truong, L. L. Cummins, Anal. Biochem. 235, 36–43 (1996). This method includes a membrane dialysis for removing salt residues as a further processing step after the extraction. The samples can only then be employed for capillary electrophoretic analysis. The low rate of retrieval of approximately 40% and the fact that it is limited to the isolation of oligonucleotides with more than 15 nucleotide units are disadvantageous with this method.

For some applications with larger DNA fragments it is necessary to extract these from complex buffer systems and solutions containing enzymes. Thus, for example, aside from polymerases and buffer salts, a PCR reaction often contains certain detergents that are required for stabilizing the enzyme. Classically, the separation of nucleic acids from aqueous solutions occurs by means of phenol extraction or by precipitation with ethanol. The use of inorganic carrier materials based on silica gel for extracting nucleic acids with a length of 40 base pairs to 50 kilobases is described, for example, in WO 9521177-A1. The adsorptive binding of nucleic acids to the glass surface occurs at a pH value smaller than 7.5 in the presence of high salt concentrations with addition of a chaotropic salt. The release of the bound nucleic acids is achieved by decreasing the ionic strength. The isolation of a plasmid from cell lysates using extraction columns that contain the two adsorbents—an ion exchange resin and silica gel—in two different segments is described in DE 4139664-A1. In this case, the nucleic acids to be isolated are first applied to the anion exchanger segment with a buffer of low ionic strength, washed and subsequently eluted onto the silica gel segment with a buffer of high ionic strength. After a further wash step, the nucleic acids are eluted with buffers of lower ionic strength.

The use of magnetic microparticles for separating polynucleotides is described in EP 281390-A2, for example. In this case, binding occurs over an amino group of the carrier material in phosphate buffer containing detergent. After magnetic separation of the charged particles, the nucleic acids are released by addition of phosphate buffer containing 50% formamide.

DESCRIPTION OF THE INVENTION

An object of the present invention was to develop a simple and inexpensive method for isolating anionic organic substances from aqueous systems. The term aqueous system here means a system in which water is a component, usually the main component, for example diluted solutions, biological media and complex buffer systems. The method is suitable for extracting low molecular compounds with anionic character such as, for example, phenol derivatives, as well as for isolating high molecular, polyanionic substances such as, for example, peptides, nucleic acids and their derivatives.

The fundamental principle of the method is based on the use of cationic polymer nanoparticles with covalently bound pH sensitive groups, especially terminal groups. The selective binding of the substances to be isolated to the particles is ensured by the cooperation of two interaction forces that are independent of each other, electrostatic and hydrophobic interactions. The affinity of the present substances for the particle surface is dependent on its anionic character as well as on its hydrophobicity. This combination permits a selective separation of the substances to be isolated from complex mixtures and highly diluted solutions by suitable selection of the extraction and wash conditions. Basic groups present on the particle surface bring about the electrostatic interactions. This part of the interaction forces can be influenced by alterations in the pH value of the medium. Thereby, the substances bound to the particle can be selectively released after their isolation by abolishing the electrostatic interactions. This allows the provision of a method for isolating anionic organic substances from aqueous systems, characterized in that these substances are reversibly bound to cationic polymer nanoparticles and are released again, after the extraction, by altering the pH value of the dispersion medium.

Hence, a method for isolating organic substances with anionic character from aqueous systems is made available according to the invention in which these substances are reversibly bound to polymer nanoparticles in cationic, protonated form, the charged polymer nanoparticles are separated from the aqueous system and the organic substances are released again from the charged polymer nanoparticles in a medium with a pH value at which the cationic polymer nanoparticles are deprotonated.

MODES TO CARRY OUT THE INVENTION

The method according to the invention comprises the use of nanoparticles with a particle size of 50 nm to 2 µm that are synthesized from vinyl monomeric units such as, for example, styrene or styrene derivatives, acrylic acid derivatives, methacrylic derivatives or mixtures thereof and additionally carry basic groups. The concentration of the basic functional groups on the particle surface is preferably more than 0.1 $\mu mol/m^2$.

The polymer nanoparticles form a dispersion in aqueous media. They contain covalently bound pH sensitive basic groups, preferably terminal groups. Examples for such groups are groups containing nitrogen, particularly aromatic or aliphatic amino, imino or amidino or guanidino groups. The production of the polymer nanoparticles used according to the invention can occur according to methods as they are disclosed in, for example, WO98/17317, in J. Colloid and Interface Sci. 195, 272–288 (1997), in Kolloid-Z. Z. Polym. 239, 677 (1979) and in the works of Goodwin et al. (Colloid Polym. Sci., 525, 464 (1974), Br. Polym. J. 10, 173 (1978), Colloid Polym. Sci. 257, 61 (1979)).

Furthermore, it is possible within the scope of the present invention to add stabilizers to the polymer suspension in an amount of preferably 0.01 to 5 percent by weight with respect to the solids content of the suspension for additional stearic stabilization. For this, non-ionic block copolymers with hydrophobic and hydrophilic parts, such as, for example poloxamers or poloxamines, are preferably used as stabilizers.

The reversible binding of the substances occurs in an aqueous starting system via electrostatic interactions with the pH sensitive basic surface groups that, according to a preferred embodiment have dissociation constants from $10^{-6}$ to $10^{-12}$, in combination with hydrophobic interactions with the polymer parent substance. Usually, the starting system is produced by adding the cationic polymer nanoparticles in dispersion form to the aqueous system that contains the organic substances with anionic character, wherein a dispersion is obtained again. The starting system can be adjusted to a desired pH before the actual conjugate formation (loading of the nanoparticles). The pH of the starting system must lie in a range in which the polymer nanoparticles are present in cationic form and the organic substance is at least partially dissociated.

The extraction of the substances from the corresponding media preferably occurs at temperatures from 4 to 60° C. and a pH value smaller than 11. Optionally, it can be adjusted by addition of a readily volatile acid.

Organic compounds are understood here under the term "organic substance with anionic character" (anionic organic compound) that at least partially dissociate in an aqueous system into one or more protons and an organic mono- or polyanion. In this case, for example, phenols, phenol derivatives, sulfonic acids, carboxylic acids, amino acids, peptides with one or more acidic functional groups or nucleic acids such as, for example, deoxyribonucleotides, ribonucleotides, chemically modified deoxyribonucleotides and/or ribonucleotides from a length of 5 nucleotide units, are considered as anionic organic compounds.

According to a preferred embodiment, the conjugates of the polymer nanoparticles with the corresponding substances arising in the reaction are separated from the corresponding media, for example, by centrifugation or filtration.

Depending on the type of the substance to be isolated and the composition of the medium to be separated, the separated conjugates can be washed with neutral or acidic aqueous wash solutions of different polarity as well as with pure deionized water. This purification process preferably occurs in the case of the extraction of compounds with polyanionic character such as, for example, nucleic acids from biological systems or complex buffer systems. According to a preferred embodiment, the resuspension of the charged polymer nanoparticles occurs, for example, by shaking or by short-term action of ultrasound.

The selective release (detachment) of the isolated and purified substances is achieved by adding the conjugates into a dispersion medium whose pH is altered with respect to the starting system such that a deprotonization of the basic functional groups present on the particles is achieved which results in an abolishment of the electrostatic interactions between the bound substances and the particles. Although a substantially complete deprotonization of the cationic polymer nanoparticles is preferred, it is not absolutely necessary; a pH that is sufficient to deprotonize the cationic polymer nanoparticles to the extent that the electrostatic interactions are at least considerably canceled again is sufficient.

Such a pH is preferably achieved by addition of a readily volatile base with a dissociation constant smaller than $10^{-9}$ such as ammonia for example. Therewith, contamination of the samples by foreign electrolytes is avoided such that the substances are present at high purity after isolation with the method according to the invention. By addition of small amounts of SDS and acetonitrile in the detachment step, the sensitivity of the method can be additionally increased, especially with small concentrations of the substances to be isolated (<1 µmol/l).

As compared to the existing techniques for the isolation and qualitative and quantitative analysis of low molecular organic substances with anionic character such as, for example, phenol derivatives, carboxylic acids, etc. from aqueous media, the method according to the invention has the considerably advantage that the compounds to be isolated do not have to be derivatized before the actual extraction. The binding occurs through the combination of electrostatic and hydrophobic interactions and permits a selective isolation of substances that can develop both interactions with the particle surface as a result of their chemical properties. Samples can also be extracted from highly diluted solutions therewith. Moreover, the principle of solid phase extraction permits the simple separation of the isolated substances from the ambient medium by filtration and/or centrifugation and concentration of the isolated samples.

The particular advantages of the method according to the invention for the isolation of polyanions such as, for example, nucleic acids, peptides, etc. essentially consists in the fact that the binding of these compounds is carried out directly in the corresponding medium and the addition of binding buffers is not necessary. Thus, for example, short natural oligonucleotides and/or derivatives thereof as well as high molecular polynucleotides can be directly isolated from complex aqueous media of different composition such as, for example, blood plasma and/or blood serum, cell extracts, urine or PCR reactions. As a result of the strongly adsorptive interactions between particles and polyanions, the conjugates can be washed with wash solutions of different polarity such as, for example, deionized water as well, and thereby effectively de-salted in a simple manner.

After the purification of the separated conjugates, the release of the bound substances occurs in a simple manner by alteration of the pH of the ambient medium. As compared to the existing methods, contamination of the samples with foreign electrolytes can be avoided by using readily volatile bases. For example, the methods for extracting nucleic acids developed up to now require the addition of foreign salts in order to allow the cleavage of the adsorbate from the carrier material. This combination renders the analytical examination of the isolated substances more difficult to a high degree. In contrast to this, the invention described herein has the advantage that the isolated nucleic acids can be characterized with analytical methods such as capillary gel electrophoresis (CGE) and electrospray mass spectrometry (ES-MS) that are heavily influenced by ionic impurities. The rate of retrieval of the isolated nucleic acids is between 50 and 100%.

In contrast to already existing techniques, the method according to the invention surprisingly permits the isolation of modified nucleic acids as well as very short oligonucleotides from a length of approximately 5 nucleic acid units despite several wash steps performed for purification of the conjugates.

Furthermore, a certain selectivity results through the binding of the nucleic acids to the nanoparticle that is caused by length- and modification-dependent affinity differences.

Therefore, the method according to the invention represents a new and efficient method for isolating anionic organic substances. The cooperation of electrostatic and hydrophobic interactions between the adsorbate molecules and the particle surface permit these to also be isolated at high dilution and/or from complex mixtures. After isolation and purification, the bound substances can be selectively released by an alteration in pH of the medium. The extraction can occur directly from media of different composition without a previous derivatization of the samples and/or a addition of binding buffers being necessary.

The following examples more closely illustrate the invention without limiting it.

EXAMPLE 1

For the following example, the following latex suspension is used: NSI-2-LS, polystyrene nanoparticles with ethylene bridged amidinium terminal groups, stabilized with 0.1% poloxamer 338 (w/v), diameter: 160 nm, solids content: 9.1 g/l, surface concentration of basic groups: 0.53 µmol/m$^2$.

The production of the latices used in the examples occurred according to the method of J. Colloid and Interface Sci. 195, (1997) page 273, which is incorporated herein by reference.

200 µl of the latex suspension NSI-2-LS are added to 1 ml of an aqueous solution containing adipinic acid at a concentration of 0.1 mmol/l and has a pH value of 7. The suspension is incubated over a time period of 5 min with occasional shaking. Subsequently, the obtained nanoparticle-adipinic acid conjugates are separated from the supernatant by centrifugation (24,000 g, 30 min.). The release of the bound acid occurs by addition of 200 µl of 25% ammonia, wherein succinic acid is added at the same time as an internal standard. The amount of isolated adipinic acid is determined by derivatizing the acids and subsequently quantifying this by gas chromatography. For this, a methanolic NaOH solution in approximately 4-fold equivalent excess is first added to the ammoniacal sample solution and blown off in a stream of nitrogen until dry; subsequently 50 µl of trifluoroacetic acid is added and incubated for 5 min. at 110° C. Subsequently, the solution is carefully blown off at room temperature. The derivatization occurs by addition of 50 µl of bistrimethyl silyl trisfluoroacetamide (BSTFA) at 60° C. in 30 min. In the same manner, the amount of adsorbed adipinic acid in the separated supernatant is determined for additional control. The average amount of adipinic acid determined from 3 experiments is 2.63 mg/g polymer. The rate of retrieval is 33%.

EXAMPLE 2

Analogously to Example 1, terephthalic acid is extracted from an aqueous solution with a concentration of 0.1 mmol/l using 200 µl of the latex suspension NSI-2-LS. The amount of terephthalic acid determined from 3 experiments is 0.91 mg/g polymer.

EXAMPLE 3

For the following example, the following latex suspension is used: NSI-2-LS, polystyrene nanoparticles with ethylene bridged amidinium terminal groups, stabilized with 0.1% poloxamer 338 (w/v), diameter: 160 nm, solids content: 9.1 g/l, surface concentration of basic groups: 0.53 µmol/m$^2$.

An aqueous mixture of 9 different phenol derivatives is added to 200 µl of the latex suspension NSI-2-LS. The individual components of the mixture 2,4-dinitrophenol, 2-methyl-4,6-dinitrophenol, 2,5-dinitrophenol, phenol, 4-nitrophenol, 3-nitrophenol, pentachlorophenol, 2-bromophenol, 2,6-dimethyl-4-nitrophenol, 2-nitrophenol, 2,4-dibromophenol are present at a concentration of 10 µg/ml. The suspension is incubated over a time period of 5 min with occasional shaking. Subsequently, the obtained nanoparticle-phenol conjugates are separated from the supernatant by centrifugation (24,000 g, 30 min.). The release of the bound acid occurs by addition of 200 µl of 25% ammonia. After a further centrifugation step (24,000 g, 10 min.), the isolated nitrophenol mixture found in the supernatant is chromatically analyzed by means of RP-HPLC without further derivatization. The starting mixture of the nitrophenols serves as a reference. The rates of retrieval of the individual components are 60–70%. This example represents the best mode of the invention for isolating low molecular compounds at present.

EXAMPLE 4

For the following example, the following latex suspension is used: NSI-S1-LS, polystyrene nanoparticles with ethylene bridged amidinium terminal groups, stabilized with 0.1% poloxamer 338 (w/v), diameter: 380 nm, solids content: 10 g/l, surface concentration: 0.17 µmol/m².

800 µl of 50 mmol/l Tris-HCl (pH 9) are added to 200 µl of human blood plasma which contains a phosphorothioate oligonucleotide of the sequence CTA TTA ACA ACA CAC AAC AG (ODN-1) at a concentration of 100 nmol/l. This mixture is added to 200 µl of the latex suspension NSI-S1-LS and incubated over a time period of 5 min with occasional shaking. The obtained nanoparticle-oligonucleotide conjugates are separated from the medium by centrifugation (24,000 g, 10 min.) and resuspended in 1 ml of a solution of 0.5 M acetic acid in ethanol/water 1:1 (v/v). After the separation of the wash solution by centrifugation (24,000 g, 5 min.), the conjugates are resuspended in 1 ml of deionized water and separated by repeated centrifugation. The release of the oligonucleotide occurs by addition of 200 µl of 150 µmol/l sodium dodecylsulfate (SDS) in a mixture of aqueous ammonia (25%)/ acetonitrile (60:40), wherein a $dT_{30}$ oligonucleotide is added at the same time as an internal standard. The released oligonucleotides are separated from the polymer particles by a further centrifugation step. Subsequently, the solution is centrifuged for separating particle residues that may still be present in the solution. The supernatant (approximately 80 µl) is lyophilized. The rate of retrieval is determined by capillary gel electrophoresis and is 91%. This example forms the best mode of the invention for polyanionic compounds at present.

EXAMPLE 5

For the following example, the following latex suspension is used: NSI-2-LS.

Analogously to Example 4, the oligonucleotide ODN-1 at different concentrations is extracted from human blood plasma using NSI-2-LS, wherein the first centrifugation step required 45 min. All subsequent centrifugation steps occurred over a time period of 30 min each. The following table shows the rates of retrieval determined by CGE:

| Concentration | Rate of retrieval |
| --- | --- |
| 100 nmol/l | 89% |
| 25 nmol/l | 84% |
| 10 nmol/l | 88% |
| 5 nmol/l | 64% |

EXAMPLE 6

The latex suspension NSI-2-LS is used for the following example.

Analogously to Example 5, the phosphorthioate oligonucleotide ODN-2 of the sequence $dT_{10}$ (Mw: 3125 g/mol) which is present at a concentration of 100 nmol/l in human blood plasma is extracted using 200 µl of the latex suspension NSI-2-LS. The rate of retrieval determined by CGE is 80%.

EXAMPLE 7

The latex suspension NSI-2-LS is used for the following example.

200 µl of the latex suspension NSI-2-LS are added to 1 ml of human blood plasma which contains a phosphordiester oligonucleotide ODN-3 of the sequence TTC TTG TCT GCT CTT at a concentration of 4 µmol/l and incubated over a time period of 5 min with occasional shaking. The obtained nanoparticle-oligonucleotide conjugates are separated from the medium by centrifugation (24,000 g, 30 min.) and resuspended in a solution of 0.5 M acetic acid in ethanol/water 1:1 (v/v). After the separation of the wash solution by centrifugation (24,000 g, 30 min.), the conjugates are resuspended in deionized water and separated by repeated centrifugation. The release of the oligonucleotide occurs by addition of 100 µl of 25% ammonia, wherein a $dT_{25}$ oligonucleotide (Mw: 7543 g/mol) is added at the same time as an internal standard. The released oligonucleotides are separated from the polymer particles by a further centrifugation step. Subsequently, the solution is centrifuged for separating particle residues that may still be present in the solution. The supernatant (approximately 80 µl) is lyophilized. The rate of retrieval is determined by capillary gel electrophoresis and is 86%.

EXAMPLE 8

The latex suspension NSI-2-LS is used for the following example.

Analogously to Example 5, the 3'-palmityl-modified oligonucleotide ODN-4 of the sequence $dT_{18}$, which is present at a concentration of 10 nmol/l in human blood plasma, is extracted using the latex NSI-2-LS. The rate of retrieval determined by CGE is 86%.

EXAMPLE 9

The latex suspension NSI-2-LS is used for the following example.

The discrimination of the nucleic acids as a function of their length is examined with two phosphorthioate oligonucleotides of the sequence $dT_{10}$ (ODN-5) and the sequence $dT_{20}$ (ODN-6). For this, 200 µl of the latex suspension NSI-2-LS are incubated with 1 ml of a 2 micromolar solution of the oligonucleotides in human blood plasma and processed analogously to Example 7. The evaluation by CGE resulted in rates of retrieval of 2% for ODN-5 and 67% for ODN-6.

EXAMPLE 10

Analogously to Example 7, a phosphordiester oligonucleotide of the sequence $dT_{15}$ (ODN-7), a phosphordiester oligonucleotide of the sequence TTC TTG TCT GCT CT (ODN-8) and a 3'-palmityl-mdoified oligonucleotide of the sequence TTC TTG TCT GCT CTT (ODN-9) which are present at a concentration of 4 µmol/l are each isolated from 1 ml of 100% fetal calf serum. The rates or retrieval are determined by CGE and are 71% for ODN-7, 70% for ODN-8 and 71% for ODN-9.

EXAMPLE 11

Analogously to Example 5, the oligonucleotide ODN-1, ODN-4 and a 2'-O-methyl-modified RNA strand of the sequence $U_{18}$ (ON-1) which are present at a concentration of 100 nmol/l are extracted from human urine. The rates of retrieval are 96% for ODN-1, 72% for ODN-4 and 83% for ON-1.

EXAMPLE 12

For the isolation of a plasmid pUC-13 (2.7 kb) from a PCR reaction, 200 µl of the solution containing the plasmid are diluted with 1 ml of deionized water, added to 200 µl of the latex suspension NSI-2-LS and incubated analogously to Example 7 and processed, wherein the addition of a standard is omitted. The quantification of the isolated nucleic acids occurs by determination of the optical density at 260 nm and by the densitometric evaluation of the bands of the gel electrophoresis analysis of the samples before and after the extraction. The determined rate of retrieval is approximately 50%.

What is claimed is:

1. A method for isolating organic substances with anionic character from aqueous systems comprising the steps of:
   a) reversibly binding the organic substances to non-crosslinked polymer nanoparticles in cationic, protonated form, forming charged polymer nanoparticles;
   b) separating the charged polymer nanoparticles from the aqueous system; and
   c) releasing the organic substance from the charged polymer nanoparticles in a medium with a pH value at which the cationic polymer nanoparticles are deprotonated.

2. Method according to claim 1, characterized in that the polymer nanoparticles carry pH sensitive basic surface groups with dissociation constants from $10^{-6}$ to $10^{-12}$.

3. The method according to claim 2, characterized in that the pH sensitive basic surface groups are present at a concentration of more than 0.1 µmol/m².

4. The method according to claim 1, characterized in that, in the step of binding to the cationic polymer nanoparticles, the organic substances with anionic character are present as a -mono- or polyanion and are selected from the group consisting of phenols, phenol derivatives, sulfonic acids, sulfonic acid derivatives, carboxylic acids, phosphoric acid derivatives, amino acids and peptides with one or more acidic functional groups or nucleic acids.

5. The method according to claim 1, characterized in that the binding of the cationic polymer nanoparticles to the organic substances occurs at temperatures from 4 to 60° C. and a pH value smaller than 11.

6. The method according to claim 1, characterized in that the cationic polymer nanoparticles bound to the organic substances are separated from the aqueous starting system by centrifugation or filtration.

7. The method according to claim 1, characterized in that the cationic polymer nanoparticles bound to the organic substances separated from the aqueous system are purified by treatment with neutral or acidic aqueous wash solutions of different polarity or pure water before the release of the bound substances occurs.

8. The method according to claim 1, characterized in that the bound substances are released by addition of a base after their separation and, optionally, their purification.

9. The method according to claim 8, characterized in that a readily volatile substance with a dissociation constant smaller than equal to $10^{-9}$ is used, for example an aqueous ammonia solution.

10. The method according to claim 1, characterized in that the release occurs in an aqueous medium that additionally contains anionic tensides and/or acetonitrile.

11. The method according to claim 1, characterized in that the polymer nanoparticles are stabilized by addition of 0.01 to 5 percent by weight stabilizers with respect to solids content of a polymer nanoparticle-suspension.

12. The method according to claim 4 wherein the organic substance with anionic character is selected from the group consisting of deoxyribonucleotides, ribonucleotides, chemically modified deoxyribonudleotides, and chemically modified ribonucleotides from a length of 5 nucleotide units.

* * * * *

UNITED STATES PATENT AND TRADEMARK OFFICE
CERTIFICATE OF CORRECTION

PATENT NO.    : 6,447,764 B1
DATED         : September 10, 2002
INVENTOR(S)   : Ernst Bayer et al.

It is certified that error appears in the above-identified patent and that said Letters Patent is hereby corrected as shown below:

<u>Column 10,</u>
Line 4, after "a" and before "or polyanion", please replace "-mono-" with
-- mono- --.

Signed and Sealed this

Fourth Day of February, 2003

JAMES E. ROGAN
*Director of the United States Patent and Trademark Office*